United States Patent
Nguyen et al.

(10) Patent No.: US 12,191,013 B2
(45) Date of Patent: Jan. 7, 2025

(54) RADIOLOGY REPORT EDITING METHOD AND SYSTEM

(71) Applicant: VINBRAIN JOINT STOCK COMPANY, Ha Noi (VN)

(72) Inventors: Manh Hung Nguyen, Ha Noi (VN); Vu Hoang, Ha Noi (VN); Anh Tu Nguyen, Ha Noi (VN); Steven Quoc Hung Truong, Ha Noi (VN); Huu Trung Bui, Ha Noi (VN)

(73) Assignee: VINBRAIN JOINT STOCK COMPANY, Ha Noi (VN)

( * ) Notice: Subject to any disclaimer, the term of this patent is extended or adjusted under 35 U.S.C. 154(b) by 278 days.

(21) Appl. No.: 17/901,228

(22) Filed: Sep. 1, 2022

(65) Prior Publication Data
US 2023/0096939 A1    Mar. 30, 2023

(30) Foreign Application Priority Data
Sep. 28, 2021   (VN) .............................. 1-2021-06040

(51) Int. Cl.
*G16H 15/00* (2018.01)
*G06F 40/117* (2020.01)
(Continued)

(52) U.S. Cl.
CPC ........... *G16H 15/00* (2018.01); *G06F 40/117* (2020.01); *G06F 40/166* (2020.01);
(Continued)

(58) Field of Classification Search
CPC ...... G16H 15/00; G16H 10/60; G06F 40/166; G06F 40/186; G06F 40/117; G06F 40/30;
(Continued)

(56) References Cited

U.S. PATENT DOCUMENTS

| 8,738,403 B2 * | 5/2014 | Flanagan | G16H 10/20 |
| | | | 705/2 |
| 9,043,206 B2 * | 5/2015 | Roberge | G10L 15/08 |
| | | | 704/251 |

(Continued)

OTHER PUBLICATIONS

Dat, Trinh Tan, Le Tran Anh Dang, Vu Ngoc Thanh Sang, Le Nhi Lam Thuy, and Pham The Bao, "Convolutional recurrent neural network with attention for Vietnamese speech to text problem in the operating room", May 2021, Int. J. of Intelligent Information and Database Systems, vol. 14, No. 3, pp. 294-314. (Year: 2021).*

(Continued)

*Primary Examiner* — Daniel C Washburn
*Assistant Examiner* — James Boggs
(74) *Attorney, Agent, or Firm* — Carter, DeLuca & Farrell LLP

(57) ABSTRACT

The invention provides a radiology report editing method and system. The method comprises providing a radiology report; recording a speech command from a user to generate a speech file; processing the speech file using a speech recognition model that has been trained using a speech dataset comprising Vietnamese speeches labeled with ground truth text transcriptions to generate a text command; processing the text command using a natural language understanding model that has been trained to perform a classification task and a sequence tagging task, wherein the classification task classifies the text command into an intent, and wherein the sequence tagging task tags each word in the text command with a tagging sequence indicates whether the each word express an intent, a content or a position; extracting a content to be edited, a position of a sentence to be edited in the text command based on the output of the sequence tagging task; and editing the radiology report based on the extracted content, the extracted position, and the extracted intent of the text command.

8 Claims, 3 Drawing Sheets

(51) Int. Cl.

| | |
|---|---|
| *G06F 40/166* | (2020.01) |
| *G06F 40/186* | (2020.01) |
| *G06F 40/20* | (2020.01) |
| *G06F 40/30* | (2020.01) |
| *G10L 15/06* | (2013.01) |
| *G10L 15/16* | (2006.01) |
| *G10L 15/18* | (2013.01) |
| *G10L 15/22* | (2006.01) |
| *G16H 10/60* | (2018.01) |

(52) U.S. Cl.
CPC ............ *G06F 40/186* (2020.01); *G06F 40/20* (2020.01); *G06F 40/30* (2020.01); *G10L 15/063* (2013.01); *G10L 15/16* (2013.01); *G10L 15/1815* (2013.01); *G10L 15/22* (2013.01); *G16H 10/60* (2018.01); *G10L 2015/223* (2013.01)

(58) Field of Classification Search
CPC ....... G06F 40/20; G10L 15/063; G10L 15/16; G10L 15/1815; G10L 15/22; G10L 2015/223
See application file for complete search history.

(56) References Cited

U.S. PATENT DOCUMENTS

| | | | | |
|---|---|---|---|---|
| 9,390,079 | B1* | 7/2016 | Reicher | G10L 15/22 |
| 10,706,210 | B2* | 7/2020 | Kaljurand | G06F 40/103 |
| 10,978,192 | B2* | 4/2021 | Casella dos Santos | G16H 10/60 |
| 11,342,055 | B2* | 5/2022 | Chang | G16H 20/40 |
| 2020/0090034 | A1* | 3/2020 | Ramachandran | G06F 16/23 |

OTHER PUBLICATIONS

Ghosh, Debjyoti, Can Liu, Shengdong Zhao, and Kotaro Hara, "Commanding and Re-Dictation: Developing Eyes-Free Voice-Based Interaction for Editing Dictated Text", Aug. 2020, ACM Transactions on Computer-Human Interaction (TOCHI), vol. 27, No. 4, Article 28, pp. 1-31. (Year: 2020).*

Lin, Ting-En, and Hua Xu, "A post-processing method for detecting unknown intent of dialogue system via pre-trained deep neural network classifier", Aug. 2019, Knowledge-Based Systems, vol. 186, No. 104979, pp. 1-11. (Year: 2019).*

Nguyen, Manh Hung, Vu Hoang, Tu Anh Nguyen, and Trung H. Bui, "Automatic Radiology Report Editing Through Voice", Aug. 2021, Interspeech 2021, pp. 4862-4863. (Year: 2021).*

Nguyen, Dat Quoc, and Anh Tuan Nguyen, "PhoBERT: Pre-trained language models for Vietnamese", Nov. 2020, Findings of the Association for Computational Linguistics: EMNLP 2020, pp. 1037-1042. (Year: 2020).*

Cao, Jin, Jun Wang, Wael Hamza, Kelly Vanee, and Shang-Wen Li, "Style Attuned Pre-training and Parameter Efficient Fine-tuning for Spoken Language Understanding", Oct. 2020, Interspeech 2020, pp. 1570-1574. (Year: 2020).*

Devlin, Jacob, Ming-Wei Chang, Kenton Lee, and Kristina Toutanova, "BERT: Pre-training of Deep Bidirectional Transformers for Language Understanding", Jun. 2019, 2019 Conference of the North American Chapter of the Association for Computational Linguistics: Human Language Technologies, pp. 4171-4186. (Year: 2019).*

Ghosh, Debjyoti, Pin Sym Foong, Shengdong Zhao, Di Chen, and Morten Fjeld, "EDITalk: Towards Designing Eyes-free Interactions for Mobile Word Processing", Apr. 2018, Proceedings of the 2018 Conference on Human Factors in Computing Systems (CHI 2018), pp. 1-10. (Year: 2018).*

Hammana, Imane, Luigi Lepanto, Thomas Poder, Christian Bellemare, and My-Sandra Ly, "Speech recognition in the radiology department: a systematic review", Jan. 2015, Health Information Management Journal, vol. 44, No. 2, pp. 4-10. (Year: 2015).*

Gopakumar, B., S. Wang, M. T. Khasawneh, D. Cummings, and K. Srihari, "Reengineering Radiology Transcription Process through Voice Recognition", Dec. 2008, 2008 IEEE International Conference on Industrial Engineering and Engineering Management, pp. 604-608. (Year: 2008).*

* cited by examiner

RADIOLOGY REPORT EDITING METHOD AND SYSTEM

FIELD OF THE INVENTION

Embodiments of the invention relate to a radiology report editing method and system that allow doctors to edit radiology reports through their voices.

DISCUSSION OF RELATED ART

Speech recognition technology has been used in radiology reporting for a long time [1][2]. It has proved positive effects on report producing productivity [2][3][4]. Normally, when doctors using this technology, they dictate the whole report, edit it if necessary and accept it. Some common report sentences may be dictated case by case.

Nuance Dragon Medical One, a product of Nuance Communications, [https//www.nuance.com/healthcare/provider-solutions/speech-recognition/dragon-medical-one.html] allows a user to input and edit a radiology report using speech recognition. An advantage of the product is that it allows the user to select and edit an arbitrary part of the radiology report along with other features like shortcuts. However, the product only supports English and the user needs to select the specific part of the radiology report before editing the radiology report.

CITATION LIST

Non-Patent Literature

1. L. H. Schwartz, P. Kijewski, H. Hertogen, P. S. Roossin, and R. A. Castellino, "Voice recognition in radiology reporting." *American Journal of Roentgenology*, vol. 169, no. 1, pp. 27-29, Jul. 1997, publisher: American Roentgen Ray Society. The citation is herein referred to as [1].
2. A. Al-Aiad, A. K. Momani, Y. Alnsour, and M. Alsharo, "The Impact of Speech Recognition Systems on The Productivity and The Workflow in Radiology Departments: A Systematic Review," *AMCIS 2020 TREOs*, vol. 62. The citation is herein referred to as [2].
3. D. R. Williams, S. K. Kori, B. Williams, S. J. Sackrison, H. M. Kowalski, M. G. McLaughlin, and B. S. Kuszyk, "JOURNAL CLUB: Voice Recognition Dictation: Analysis of Report Volume and Use of the Send-to-Editor Function," *American Journal of Roentgenology*, vol. 201, no. 5, pp. 1069-1074, October 2013, publisher: American Roentgen Ray Society. The citation is herein referred to as [3].
4. I. Hammana, L. Lepanto, T. Poder, C. Bellemare, and M.-S. Ly, "Speech Recognition in the Radiology Department: A Systematic Review," *Health Information Management Journal*, vol. 44, no. 2, pp. 4-10, 2015, eprint: https://doi.org/10.77/1833358150440201. The citation is herein referred to as [4].
5. S. Kriman, S. Beliaev, B. Ginsburg, J. Huang, O. Kuchaiev, V. Lavrukhin, R. Leary, J. Li, and Y. Zhang, "Quartznet: Deep automatic speech recognition with id time-channel separable convolutions," 2019. The citation is herein referred to as [5].
6. A. Graves, S. Fernandez, F. Gomez, and J. Schmidhuber, "Connec-'tionist temporal classification: Labelling unsegmented sequence data with recurrent neural 'networks," vol. 2006, 01 2006, pp. 369-376. The citation is herein referred to as [6].
7. D. Q. Nguyen and A. T. Nguyen, "Phobert: Pre-trained language models for vietnamese," *CoRR*, vol. abs/2003.00744, 2020. The citation is herein referred to as [7].

SUMMARY OF THE INVENTION

The present invention has been made to solve the above-mentioned problems, and an object of the present invention is to provide a technique capable of editing a radiology report using a user's voice in which the user can select and edit a sentence in the radiology report with a single command. The technique according to the present invention is also able to support Vietnamese language, which is used by over 100 million people around the world.

According to the first aspect of the invention, there is provided a radiology report editing method, the method comprising:

providing a radiology report to be edited;

recording a speech command from a user to generate a speech file;

processing the speech file using a speech recognition model that has been trained using a speech dataset comprising Vietnamese speeches labeled with ground truth text transcriptions to generate a text command;

processing the text command using a natural language understanding model that has been trained to perform a classification task and a sequence tagging task;

wherein the classification task classifies the text command into an intent among a plurality of intents comprising an addition intent, a modification intent, a deletion intent and an unknown intent;

wherein the sequence tagging task tags each word in the text command with a tagging sequence, wherein the tagging sequence is selected from a group comprising an intent tagging sequence, a content tagging sequence and a position tagging sequence, wherein the intent tagging sequence indicates the classified intent of the text command; the content tagging sequence indicates a content to be edited and the position tagging sequence indicates a position of a sentence to be edited in the radiology report;

extracting the content and the position in the text command based on the content tagging sequence, the position tagging sequence, respectively; and if the classified intent is not the unknown intent, editing the radiology report based on the extracted content, the extracted position, and the classified intent of the text command.

According to the second aspect of the invention, there is provided a radiology report editing system comprising one or more computers and one or more storage devices storing instructions that, when executed by the one or more computers, cause the one or more computers to perform the model training method according to the first aspect of the invention.

BRIEF DESCRIPTION OF THE DRAWINGS

The above and other objects, features and advantages of the invention will become more apparent to those of ordinary skill in the art by describing in detail exemplary embodiments thereof with reference to the attached drawings, in which.

DETAILED DESCRIPTION OF EXEMPLARY EMBODIMENTS

Figure 1:
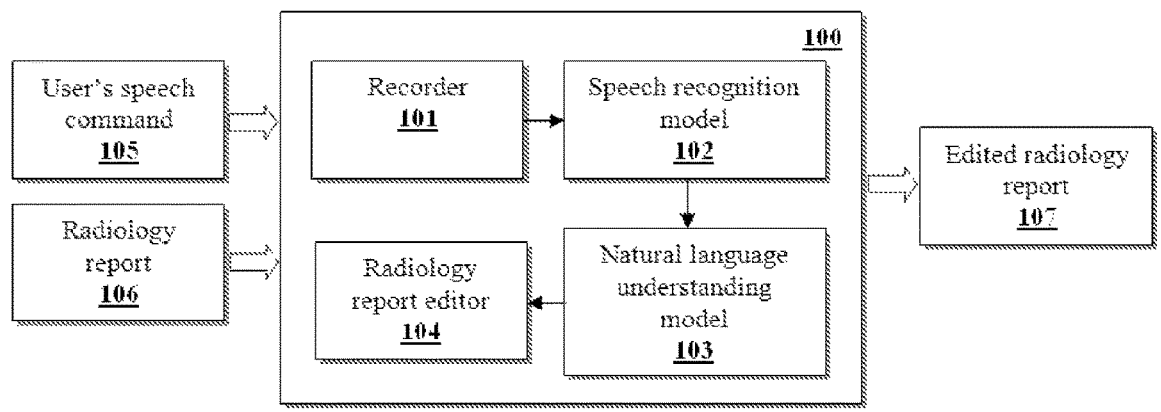
FIG. 1 shows an example radiology report editing system.

While the invention may have various modifications and alternative forms, specific embodiments thereof are shown by way of example in the drawings and will be described herein in detail. However, there is no intent to limit the invention to the particular forms disclosed. On the contrary, the invention is to cover all modifications, equivalents, and alternatives falling within the spirit and scope of the appended claims.

It should be understood that, although the terms "first," "second," and the like may be used herein to describe various elements, the elements are not limited by the terms. The terms are only used to distinguish one element from another element. For example, a first element could be termed a second element, and, similarly, a second element could be termed a first element without departing from the scope of the invention. As used herein, the term "and/or" includes any and all combinations of one or more of the associated listed items.

The terminology used herein is for the purpose of describing particular embodiments only and is not intended to be limiting to the invention. As used herein, the singular forms "a," "an," "another," and "the" are intended to also include the plural forms, unless the context clearly indicates otherwise. It should be further understood that the terms "comprise," "comprising," "include," and/or "including," when used herein, specify the presence of stated features, integers, steps, operations, elements, parts, or combinations thereof, but do not preclude the presence or addition of one or more other features, integers, steps, operations, elements, parts, or combinations thereof.

Unless otherwise defined, all terms including technical and scientific terms used herein have the same meaning as commonly understood by one of ordinary skill in the art to which this invention belongs. It should be further understood that terms, such as those defined in commonly used dictionaries, should be interpreted as having a meaning that is consistent with their meaning in the context of the relevant art and are not to be interpreted in an idealized or overly formal sense unless expressly so defined herein.

Hereinafter, embodiments will be described in detail with reference to the accompanying drawings, the same or corresponding components are denoted by the same reference numerals regardless of reference numbers, and thus the description thereof will not be repeated.

And throughout the detailed description and claims of the present disclosure, the term "training/trained" or "learning/learned" refers to performing machine learning through computing according to a procedure. It will be appreciated by those skilled in the art that it is not intended to refer to a mental function such as human educational activity.

As used herein, a model is trained to output a predetermined output with respect to a predetermined input, and may include, for example, neural networks. A neural network refers to a recognition model that simulates a computation capability of a biological system using a large number of artificial neurons being connected to each other through edges.

The neural network uses artificial neurons configured by simplifying functions of biological neurons, and the artificial neurons may be connected to each other through edges having connection weights. The connection weights, parameters of the neural network, are predetermined values of the edges, and may also be referred to as connection strengths. The neural network may perform a cognitive function or a learning process of a human brain through the artificial neurons. The artificial neurons may also be referred to as nodes.

A neural network may include a plurality of layers. For example, the neural network may include an input layer, a hidden layer, and an output layer. The input layer may receive an input to be used to perform training and transmit the input to the hidden layer, and the output layer may generate an output of the neural network based on signals received from nodes of the hidden layer. The hidden layer may be disposed between the input layer and the output layer. The hidden layer may change training data received from the input layer to an easily predictable value. Nodes included in the input layer and the hidden layer may be connected to each other through edges having connection weights, and nodes included in the hidden layer and the output layer may also be connected to each other through edges having connection weights. The input layer, the hidden layer, and the output layer may respectively include a plurality of nodes.

Hereinafter, training a neural network refers to training parameters of the neural network. Further, a trained neural network refers to a neural network to which the trained parameters are applied.

The neural network may be trained through supervised learning or unsupervised learning. Supervised learning refers to a method of providing input data and label corresponding thereto to the neural network, while in unsupervised learning, the input data provided to the neural network does not contain label.

The term "radiology report" is a report generated by a radiologist in interpreting one or more radiographic images of a patient. The radiographic images may be MRI (Magnetic resonance imaging) images, CT (computed tomography) images, X-ray images, etc.

FIG. 1 is a block diagram of an example radiology report editing system 100 for editing a radiology report according to an embodiment of the invention. The radiology report editing system 100 is an example of a system implemented as computer programs on one or more computers in one or more locations in which the systems, components, and techniques described below are implemented.

The radiology report editing system 100 receives a speech command 105 from a user to delete, modify or add an arbitrary whole sentence in a radiology report 106. According to an embodiment, the radiology report 106 is in Vietnamese. The radiology report editing system 100 comprises a recorder 101, a speech recognition model 102, a natural language understanding model 103 and a radiology report editor 104.

The recorder 101 records the speech command 105 from the user to generate a speech file. According to an embodiment, the recorder 101 further transforms the time series audio signal, which is a sequence of sound pressure over time, stored in the speech file to a mel spectrogram, which shows the evolution of the mel frequency spectrum in time. Then, the speech file that has been transformed is input into the speech recognition model 102 for further processing.

The speech recognition model 102 processes the speech file to generate a text command from the speech file.

According to an embodiment, the speech recognition model 102 employs the architecture of an adapted QuartzNet [5] for Vietnamese. According to the embodiment, the speech recognition model 102 comprises a 1D (one dimension) convolution layer, followed by 5 (five) groups of blocks and 3 (three) additional 1D convolution layers. Each block has 5 (five) identical modules, each module comprises a depthwise convolution layer, a pointwise convolution layer, a normalization layer and a ReLU (Rectified Linear Unit) layer. There is a residual connection between the blocks. Each block is repeated 3 times.

The speech recognition model 102 has been trained using a speech dataset comprising Vietnamese speeches labeled with ground truth text transcriptions. According to an embodiment, the speech recognition model 102 is trained with the Connectionist Temporal Classification (CTC) loss [6].

The speech dataset for training the speech recognition model 102 includes two parts, wherein the first part includes speeches in general language and the second part includes speeches in radiology. According to an embodiment the speech dataset is a private dataset comprises about 11,000 hours of speeches in general language and additional 95 hours of speeches for radiology. There is a total of about 44,000 voices which are representative for all regional areas, gender, and a large range of ages.

According to an embodiment, the speech recognition model 102 achieves 3.69% Word Error Rate (WER) for the Vietnamese radiology language in a held-out test set.

The natural language understanding model 103 is trained to processes the text command to perform a classification task and a sequence tagging task.

In particular, the classification task classifies the text command into an intent among a plurality of intents. The plurality of intents comprises an addition intent, a modification intent, a deletion intent and an unknown intent. The addition intent means the intent of the text command to add some contents to the radiology report 106. The modification intent means the intent of the text command to modify some contents of the radiology report 106. The deletion intent means the intent of the text command to delete some contents in the radiology report 106. The unknown intent means that there is no intent in the text command or it cannot be determined the intent of the text command.

The sequence tagging task tags each word in the text command with a tagging sequence. The tagging sequence is selected from a group comprising an intent tagging sequence, a content tagging sequence and a position tagging sequence. The intent tagging sequence indicates the classified intent of the text command including the addition intent, the modification intent, the deletion intent and the unknown intent. The content tagging sequence indicates a content to be edited. The position tagging sequence indicates a position of the sentence to be edited in the radiology report.

The natural language understanding model 103 is trained using a training dataset. The training dataset includes a plurality of text commands that are generated based on a plurality of sentences extracted from a plurality of radiology reports. According to an embodiment, the plurality of sentences comprises about 340,000 sentences extracted from the plurality of radiology reports. The plurality of text commands represent a plurality of intents comprising an addition intent, a modification intent, a deletion intent and an unknown intent. In particular, the plurality of text commands are generated as follows.

i) A template is provided. The template is selected from a group of an addition template, a modification template and a deletion template that represent an expression manner in Vietnamese for the addition intent, the modification intent or the deletion intent, respectively.

ii) Data originated from the plurality of sentences is filled into the template to create a first text command, wherein the filled-in data comprise a content to be input and a position of a sentence in the radiology report to be edited. In particular, the data is filled into the addition template to generate the first text command representing the addition intent. The data is filled into the modification template to generate the first text command representing the modification intent. The data is filled into the deletion template to generate the first text command representing the deletion intent.

iii) Each sentence in the plurality of sentences is classified as a second text command that represents the unknown intent.

Table 1 shows some examples of text commands for training the natural language understanding model 103.

TABLE 1

| Command | Content | Intent | Position |
| --- | --- | --- | --- |
| Add normal mediastinum after the first sentence | Normal mediastinum | Addition | After the first sentence |
| Change the third sentence to enlarged cardiomegaly | Enlarged cardiomegaly | Modification | The third sentence |
| Delete the fourth sentence | | Deletion | The fourth sentence |

In the first example, the addition template is used. The full text command is a combination of the addition template and the filled-in data, namely, Add+[content (i.e., *Normal mediastinum*)]+[position (i.e., *After the first sentence*)].

In the second example, the modification template is used. The full text command is a combination of the modification template and the filled-in data, namely, Change+[position (i.e., *The third sentence*)]+[content (i.e., *Enlarged cardiomegaly*)]. Another modification template used in this case may be Change+[content]+[position].

In the third example, the deletion template is used. The full text command is a combination of the deletion template and the filled-in data, namely, Delete+[content (*in this case, no content is necessary*)]+[position (i.e., *The fourth sentence*)].

Figure 2:
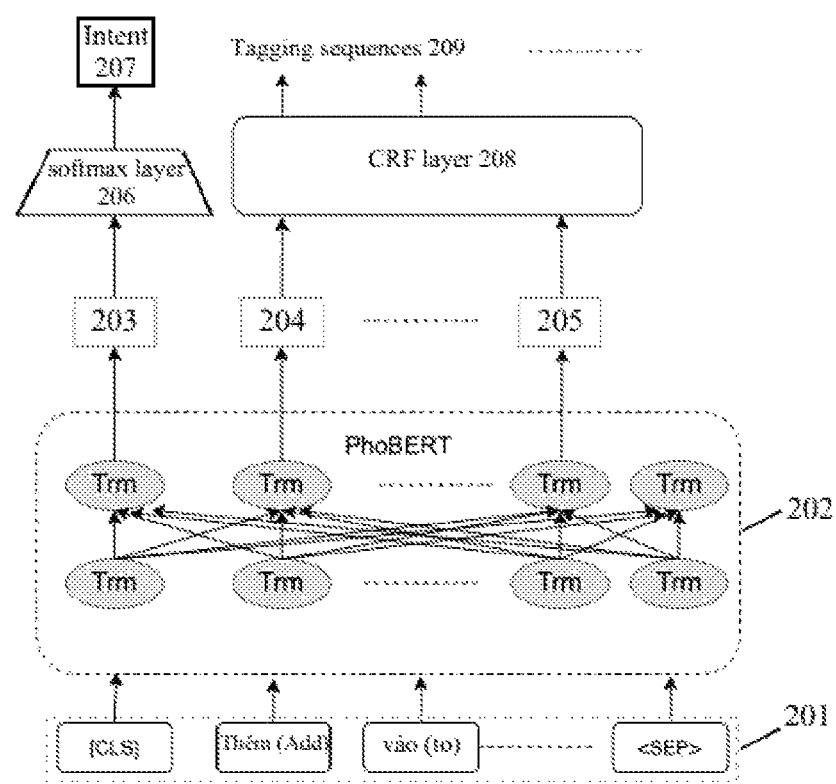
FIG. 2 illustrates the architecture of a natural language understanding model of the radiology report editing system.

FIG. 2 illustrates the architecture of the natural language understanding model 103. In particular, the natural language understanding model 103 comprises a BERT (Bidirectional Encoder Representations from Transformers)-based model 202 that has been pre-trained for Vietnamese; a softmax layer 206; and a conditional random field (CRF) layer 208. According to an embodiment, the BERT-based model 202 is PhoBERT [7].

The classification task and the sequence tagging task are jointly trained using the BERT-based model. Specifically, the classification task is trained using the BERT-based model and the softmax layer; while the sequence tagging task is trained using the BERT-based model and the CRF layer. The following describes the training of the classification task and the sequence tagging task.

i) An input text command is tokenized to generate a tokenized sequence of a plurality of tokens 201 that comprises a plurality of word tokens, a classification [CLS] token and a separator [SEP] token. The [CLS] token and the [SEP] token are added to the beginning and the end of the tokenized sequence, respectively. In FIG. 2, the word tokens are "Thêm (Add)", "vào (to)", etc.

ii) The BERT-based model 202 processes the plurality of tokens 201 to generate a [CLS] token representation 203 that is an aggregate of entire input representations of the input text command and a plurality of representations 204, 205, . . . for the plurality of word tokens. In FIG. 2, Trm are the intermediate representations of the plurality of tokens 201.

iii) The [CLS] token representation 203 is fed to the softmax layer 206 to predict an intent 207 of the input text command. For example, the predicted intent 207 in this case is the addition intent in FIG. 2.

iv) The plurality of representations 204, 205, . . . for the plurality of word tokens are classified into a plurality of tags and the plurality of tags are fed to the CRF layer 208 to obtain the plurality of tagging sequences 209.

v) A first loss measuring a difference between the predicted intent 207 and a ground truth intent of the input text command is minimized.

vi) A second loss measuring a difference between the obtained plurality of tagging sequences 209 and ground truth tagging sequences of the word tokens is minimized.

After the natural language understanding model 103 has been trained, it can be used to perform the classification task and the sequence tagging task.

Refer back to FIG. 1, the radiology report editor 104 extracts the content and the position in the text command based on the content tagging sequence, the position tagging sequence, respectively.

If the classified intent is not the unknown intent, the radiology report editor 104 edits the radiology report based on the extracted content, the extracted position, and the classified intent of the text command. The output of the radiology report editing system 100 is an edited radiology report 107 that has been edited from the user's speech command 105.

If the classified intent is the unknown intent, no action is taken.

Figure 3:
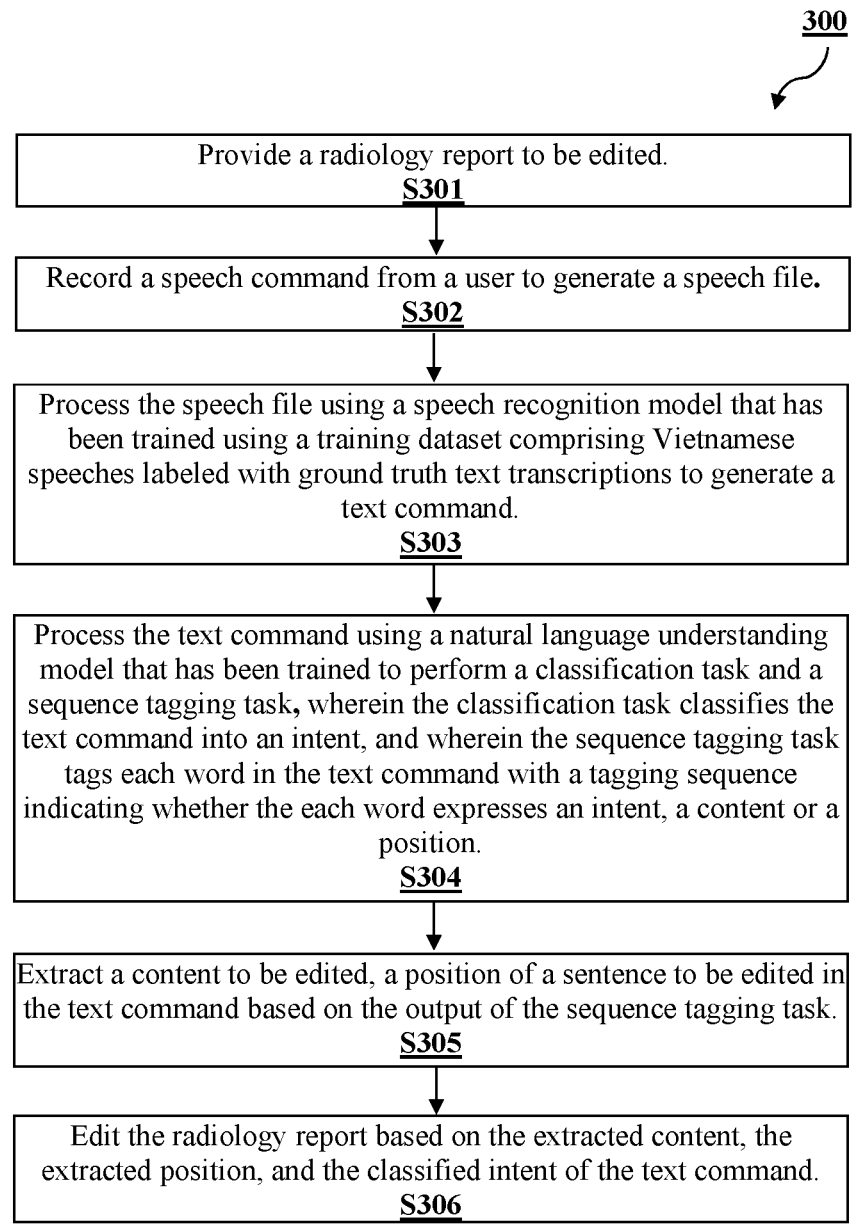
FIG. 3 is a flow diagram of an example process for editing a radiology report.

FIG. 3 is a flow diagram of an example process 300 for editing a radiology report based on a user's speech command. For convenience, the process 300 will be described as being performed by a system of one or more computers located in one or more locations. For example, a radiology report editing system, e.g., the radiology report editing system 100 (herein after referred to as "the system") of FIG. 1, appropriately programmed, can perform the process 300.

In step S301, the system provides a radiology report to be edited (for example, the radiology report 106 of FIG. 1). According to an embodiment, the radiology report is in Vietnamese.

In step S302, the system records a speech command (for example, the speech command 105 of FIG. 1) from a user to generate a speech file. In this step, the system further transforms the time series audio signal, which is a sequence of sound pressure over time, stored in the speech file to a mel spectrogram, which shows the evolution of the mel frequency spectrum in time.

In step S303, the system processes the speech file using a speech recognition model (for example, the speech recognition model 102 of FIG. 1) that has been trained using a speech dataset comprising Vietnamese speeches labeled with ground truth text transcriptions to generate a text command.

The speech dataset for training the speech recognition model includes two parts, wherein the first part includes speeches in general language and the second part includes speeches in radiology.

The architecture and the training of the speech recognition model are described in the corresponding description of FIG. 1, so the detailed description thereof is omitted for brevity.

In step S304, the system processes the text command using a natural language understanding model (for example, the natural language understanding model 103 of FIG. 1) to perform a classification task and a sequence tagging task, wherein the classification task classifies the text command into an intent, and wherein the sequence tagging task tags each word in the text command with a tagging sequence indicating whether the each word expresses an intent, a content or a position.

In particular, in the classification task, the system classifies the text command into the intent among a plurality of intents. The plurality of intents comprises an addition intent, a modification intent, a deletion intent and an unknown intent. The addition intent means the intent of the text command to add some contents to the radiology report. The modification intent means the intent of the text command to modify some contents of the radiology report. The deletion intent means the intent of the text command to delete some contents in the radiology report. The unknown intent means that there is no intent in the text command or it cannot determine the intent of the text command.

In the sequence tagging task, the system tags the each word in the text command with the tagging sequence that is selected from a group comprising an intent tagging sequence, a content tagging sequence and a position tagging sequence. The intent tagging sequence indicates the classified intent of the text command including the addition intent, the modification intent, the deletion intent and the unknown intent. The content tagging sequence indicates a content to be edited. The position tagging sequence indicates a position of a sentence to be edited in the radiology report.

The natural language understanding model is trained using a training dataset. The training dataset includes a plurality of text commands that are generated based on a plurality of sentences extracted from a plurality of radiology reports. The plurality of text commands represent a plurality of intents comprising an addition intent, a modification intent, a deletion intent and an unknown intent. In particular, the plurality of text commands are generated as follows.

i) A template is provided. The template is selected from a group of an addition template, a modification template and a deletion template that represent an expression manner in Vietnamese for the addition intent, the modification intent or the deletion intent, respectively.

ii) Data originated from the plurality of sentences is filled into the template to create a first text command wherein the filled-in data comprise a content to be input and a position of a sentence in the radiology report to be edited. In particular, the data is filled into the addition template to generate the first text command representing the addition intent. The data is filled into the modification template to generate the first text command representing the modification intent. The data is filled into the deletion template to generate the first text command representing the deletion intent.

iii) Each sentence in the plurality of sentences is classified as a second text command that represents the unknown intent.

The architecture of the natural language understanding model and the training of the natural language understanding model are described in the description of FIG. 2, so the detailed description thereof is omitted for brevity.

In step S305, the system extracts the content to be edited, the position of the sentence to be edited in the text command based on the output of the sequence tagging task. In particular, the system extracts the content to be edited and the position to be edited in the text command based on the content tagging sequence, the position tagging sequence, respectively.

In step S306, the system edits the radiology report based on the extracted content, the extracted position, and the classified intent of the text command. In particular, if the classified intent is not the unknown intent, the system edits the radiology report based on the extracted content, the extracted position, and the classified intent of the text command.

If the classified intent is the unknown intent, the system performs no action.

For a system of one or more computers to be configured to perform particular operations or actions means that the system has installed on it software, firmware, hardware, or a combination of them that in operation cause the system to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a relationship graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

The invention claimed is:

1. A radiology report editing method:
    providing a radiology report to be edited;
    recording a speech command from a user to generate a speech file;
    processing the speech file using a speech recognition model that has been trained using a speech dataset comprising Vietnamese speeches labeled with ground truth text transcriptions to generate a text command;
    processing the text command using a natural language understanding model that has been trained to perform a classification task and a sequence tagging task;
        wherein the classification task classifies the text command into an intent among a plurality of intents comprising an addition intent, a modification intent, a deletion intent and an unknown intent;
        wherein the sequence tagging task tags each word in the text command with a tagging sequence, wherein the tagging sequence is selected from a group comprising an intent tagging sequence, a content tagging sequence and a position tagging sequence, wherein the intent tagging sequence indicates the classified intent of the text command; the content tagging sequence indicates a content to be edited and the position tagging sequence indicates a position of a sentence to be edited in the radiology report;
    extracting the content and the position in the text command based on the content tagging sequence, the position tagging sequence, respectively;
    if the classified intent is not the unknown intent, editing the radiology report based on the extracted content, the extracted position, and the classified intent of the text command;
    wherein the natural language understanding model is trained using a training dataset,
    wherein the training dataset includes a plurality of text commands that are generated based on a plurality of sentences extracted from a plurality of radiology reports,
    wherein the plurality of text commands represents a plurality of intents comprising an addition intent, a modification intent, a deletion intent and an unknown intent;
    wherein the plurality of text commands are generated using operations of:
    providing a template that is selected from a group of an addition template, a modification template and a deletion template that represent an expression manner in Vietnamese for the addition intent, the modification intent or the deletion intent, respectively; and
    filling data originated from the plurality of sentences into the template to create a first text command wherein the filled-in data comprise a content to be input and a position of a sentence in the radiology report to be edited.

2. The radiology report editing method of claim 1,
    wherein the plurality of text commands are generated further using an operation of classifying each sentence in the plurality of sentences as a second text command representing the unknown intent.

3. The radiology report editing method of claim 2, wherein the natural language understanding model comprises:
    a BERT (Bidirectional Encoder Representations from Transformers)-based model that has been pre-trained for Vietnamese;
    a softmax layer; and
    a conditional random field (CRF) layer;
    wherein the classification task and the sequence tagging task are jointly trained using the BERT-based model;
    wherein the classification task is trained using the BERT-based model and the softmax layer; and wherein the sequence tagging task is trained using the BERT-based model and the CRF layer.

4. The radiology report editing method of claim 3, wherein the classification task and the sequence tagging task are jointly trained using the operations of:
   tokenizing an input text command to generate a tokenized sequence of a plurality of tokens that comprises a plurality of word tokens, a classification [CLS] token and a separator [SEP] token; wherein the [CLS] token and the [SEP] token are added to the beginning and the end of the tokenized sequence, respectively;
   processing the plurality of tokens using the BERT-based model to generate a [CLS] token representation that is an aggregate of entire input representation of the input command and a plurality of representations for the plurality of word tokens;
   feeding the [CLS] token representation to the softmax layer to predict an intent of the input text command;
   classifying the plurality of representations for the plurality of word tokens into a plurality of tags and feeding the plurality of tags to the CRF layer to obtain the plurality of tagging sequences;
   minimizing a first loss measuring a difference between the predicted intent and a ground truth intent of the input text command; and
   minimizing a second loss measuring a difference between the obtained plurality of tagging sequences and ground truth tagging sequences of the word tokens.

5. The radiology report editing method of claim 4, wherein the recording of the speech command comprising transforming a time series audio signal stored in the speech file into a mel spectrogram.

6. The radiology report editing method of claim 5, wherein the speech dataset for training the speech recognition model includes two parts, wherein the first part includes speeches in general language and the second part includes speeches in radiology.

7. The radiology report editing method of claim 6, wherein the radiology report is in Vietnamese.

8. A radiology report editing system comprising one or more computers and one or more storage devices storing instructions that when executed by the one or more computers cause the one or more computers to perform operations comprising:
   providing a radiology report to be edited;
   recording a speech command from a user to generate a speech file;
   processing the speech file using a speech recognition model that has been trained using a speech dataset comprising Vietnamese speeches labeled with ground truth text transcriptions to generate a text command;
   processing the text command using a natural language understanding model that has been trained to perform a classification task and a sequence tagging task;
      wherein the classification task classifies the text command into an intent among a plurality of intents comprising an addition intent, a modification intent, a deletion intent and an unknown intent;
      wherein the sequence tagging task tags each word in the text command with a tagging sequence, wherein the tagging sequence is selected from a group comprising an intent tagging sequence, a content tagging sequence and a position tagging sequence, wherein the intent tagging sequence indicates the classified intent of the text command; the content tagging sequence indicates a content to be edited and the position tagging sequence indicates a position of a sentence to be edited in the radiology report;
   extracting the content and the position in the text command based on the content tagging sequence, the position tagging sequence, respectively;
   if the classified intent is not the unknown intent, editing the radiology report based on the extracted content, the extracted position, and the classified intent of the text command;
   wherein the natural language understanding model is trained using a training dataset,
   wherein the training dataset includes a plurality of text commands that are generated based on a plurality of sentences extracted from a plurality of radiology reports,
   wherein the plurality of text commands represents a plurality of intents comprising an addition intent, a modification intent, a deletion intent and an unknown intent;
   wherein the plurality of text commands are generated using operations of:
   providing a template that is selected from a group of an addition template, a modification template and a deletion template that represent an expression manner in Vietnamese for the addition intent, the modification intent or the deletion intent, respectively; and
   filling data originated from the plurality of sentences into the template to create a first text command wherein the filled-in data comprise a content to be input and a position of a sentence in the radiology report to be edited.

* * * * *